United States Patent [19]

Krämer et al.

[11] 4,154,842

[45] May 15, 1979

[54] FUNGICIDALLY AND BACTERICIDALLY ACTIVE 1-AZOLYL-4-HYDROXY-1-PHENOXY-BUTANE DERIVATIVES

[75] Inventors: Wolfgang Krämer; Karl H. Büchel, both of Wuppertal; Paul-Ernst Frohberger, Leverkusen; Peter Kraus, Cologne, all of Fed. Rep. of Germany

[73] Assignee: Bayer Aktiengesellschaft, Leverkusen, Fed. Rep. of Germany

[21] Appl. No.: 819,534

[22] Filed: Jul. 27, 1977

[30] Foreign Application Priority Data

Aug. 7, 1976 [DE] Fed. Rep. of Germany ....... 2635666

[51] Int. Cl.² .................. A01N 9/22; A01N 21/00; C07D 233/60; C07D 249/08
[52] U.S. Cl. .................................. 424/269; 260/308 R; 260/456 R; 260/456 P; 260/465 D; 260/590 R; 424/232; 424/273 R; 548/341; 560/20; 560/32; 560/106; 560/254
[58] Field of Search ................... 260/308 R; 424/269, 424/273, 232; 548/341

[56] References Cited

U.S. PATENT DOCUMENTS

| 3,796,704 | 3/1974 | Metzger et al. ...................... 260/309 |
| 3,812,142 | 5/1974 | Meiser et al. ........................ 548/341 |
| 3,952,002 | 4/1976 | Kramer et al. .................. 260/308 A |
| 4,005,083 | 1/1977 | Büchel et al. ....................... 424/273 |
| 4,038,404 | 7/1977 | Meiser et al. ........................ 424/269 |

*Primary Examiner*—Alton D. Rollins
*Attorney, Agent, or Firm*—Sprung, Felfe, Horn, Lynch & Kramer

[57] ABSTRACT

1-Azolyl-4-hydroxy-1-phenoxy-butane derivatives of the formula

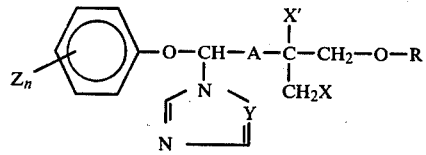

in which
R is hydrogen, —CO—$R^1$ or —$SO_2$—$R^2$,
$R^1$ is cycloalkyl, alkylamino, dialkylamino, alkenyl, alkynyl, or optionally substituted alkyl, phenyl, phenoxyalkyl, phenylalkyl or phenylamino,
$R^2$ is alkyl or optionally substituted phenyl,
A is —CO— or CH(OH),
X is H or —OR,
$X^1$ is alkyl or optionally substituted phenyl,
Y is CH or N,
Z is halogen, alkyl, halogenoalkyl, cycloalkyl, alkoxy, alkylthio, alkoxycarbonyl, amino, cyano, nitro, or optionally substituted phenyl, phenoxy or phenylalkyl, and
n is 0, 1, 2, 3, 4 or 5, or a salt thereof, which possess fungicidal and bactericidal properties.

11 Claims, No Drawings

FUNGICIDALLY AND BACTERICIDALLY ACTIVE 1-AZOLYL-4-HYDROXY-1-PHENOXY-BUTANE DERIVATIVES

The present invention relates to and has for its objects the provision of particular 1-azolyl-4-hydroxy-1-phenoxy-butane derivatives which possess fungicidal and bactericidal properties, active compositions in the form of mixtures of such compounds with solids and liquid dispersible carrier vehicles, and methods for producing such compounds and for using such compounds in a new way especially for combating pests, e.g. fungi and bacteria, with other and further objects becoming apparent from a study of the within specification and accompanying examples.

It has been disclosed in U.S. Pat. No. 3,898,341 and DOS No. 1,795,249 that certain trityl-1,2,4-triazoles, such as triphenyl-(1,2,4-triazol-1-yl)-methane, and certain 3,3-dimethyl-1-(imidazol-1-yl)-1-phenoxy-butan-2-ones substituted in the phenyl part, such as 2,5-dichlorophenoxy-3,3-dimethyl-1-(imidazol-1-yl)-butan-2-one, exhibit fungicidal activity. However, their action is not always entirely satisfactory, especially if low amounts and low concentrations are used.

The present invention now provides, as new compounds, the 1-azolyl-4-hydroxy-butane derivatives of the general formula

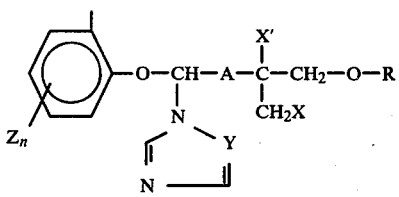

in which

R is hydrogen, —CO—R$^1$ or —SO$_2$—R$^2$,

R$^1$ is optionally substituted alkyl, alkenyl, alkynyl, optionally substituted phenyl, optionally substituted phenoxyalkyl, optionally substituted phenylalkyl, cycloalkyl, alkylamino, dialkylamino or optionally substituted phenylamino, R$^2$ is alkyl or optionally substituted phenyl, A is —CO— or —CH(OH)—, X is hydrogen or —OR, X$^1$ is alkyl or optionally substituted phenyl, Y is the CH group or N, Z is halogen, alkyl, halogenoalkyl, cycloalkyl, alkyl, alkoxy, alkylthio, alkoxycarbonyl, optionally substituted phenyl, optionally substituted phenoxy, optionally substituted phenylalkyl, amino, cyano, or nitro, and n is 0, 1, 2, 3, 4 or 5, and their salts.

Preferably, R represents hydrogen, an acyl radical —CO—R$^1$ or a grouping —SO$_2$—R$^2$, R$^1$ represents straight-chain or branched alkyl with 1 to 18 carbon atoms (which is optionally substituted by halogen, amino, acetylamino, alkoxy with 1 to 4 carbon atoms, or alkoxycarbonyl with 1 to 4 carbon atoms in the alkyl part), alkenyl with 2 to 6 carbon atoms, alkynyl with 2 to 6 carbon atoms, cycloalkyl with 5 to 7 carbon atoms, phenyl or phenylalkyl or phenoxyalkyl in each case with 1 to 4 carbon atoms in the alkyl part (the last three radicals being optionally substituted in the phenyl part by halogen, amino, cyano, nitro or alkyl with 1 to 2 carbon atoms), alkylamino or dialkylamino with 1 to 4 carbon atoms in each alkyl part, or phenylamino, which is optionally substituted by halogen, nitro or cyano; and R$^2$ represents straight-chain or branched alkyl with 1 to 4 carbon atoms, or phenyl which is optionally substituted by halogen, amino, cyano, nitro or alkyl with 1 to 2 carbon atoms;

X$^1$ represents alkyl with 1 or 2 carbon atoms or phenyl which is optionally substituted by halogen (especially fluorine, chlorine or bromine) or by alkyl with 1 to 2 carbon atoms;

Z represents halogen, straight-chain or branched alkyl with 1 to 4 carbon atoms, cycloalkyl with 5 to 7 carbon atoms (especially cyclohexyl), halogenoalkyl with 1 or 2 carbon atoms and 1 to 5 halogen atoms (especially fluorine and chlorine atoms, the trifluoromethyl group being an example), alkoxy or alkylthio each with 1 or 2 carbon atoms, alkoxycarbonyl with 1 to 5 carbon atoms in the alkoxy part, amino, cyano, nitro, phenyl or phenoxy (either of which is optionally substituted by halogen, amino, cyano, nitro or alkyl with 1 to 2 carbon atoms), or phenylalkyl with 1 or 2 carbon atoms in the alkyl part, alkylcarbonyl with a total of up to 3 carbon atoms being an optional substituent in the alkyl part and halogen (namely fluorine, chlorine, bromine or iodine), nitro or cyano being an optional substituent in the phenyl part;

n represents 0, 1, 2 or 3; and

X represents hydrogen or an OR grouping,

Those compounds of the formula (I) in which A represents the CH(OH) group, possess two asymmetrical carbon atoms and can therefore exist as the two geometrical isomers (erythro-form and threo-form), which may be formed in varying ratios. In both cases, they exist as optical isomers. All isomers are intended to be covered by the formula (I).

The 1-azolyl-4-hydroxy-butane derivatives obtainable according to the invention can be converted to the salts by reaction with acids. Conversely, the acid addition salts can be converted into the free bases by treatment with suitable bases.

From the point of view of phyto-toxicity, the preferred salts of the compounds of the formula (I) are physiologically tolerated salts, these being in general salts with physiologically tolerated acids. The preferred acids include the hydrogen halide acids (for example hydrobromic acid and especially hydrochloric acid), phosphoric acid, nitric acid, monofunctional or difunctional carboxylic acids and hydroxycarboxylic acids (for example acetic acid, maleic acid, succinic acid, fumaric acid, tartaric acid, salicylic acid, citric acid, sorbic acid and lactic acid) and 1,5-naphthalene-disulphonic acid.

Surprisingly, the active compounds according to the invention exhibit a substantially greater fungicidal activity, especially against cereal diseases, than the compounds triphenyl-(1,2,4-triazol-1-yl)-methane and 2,5-dichlorophenoxy-3,3-dimethyl-1-(imidazol-1-yl)-butan-2-one known from the state of the art, which, chemically and in respect of their action, are closely related compounds. Their additional bactericidal action is equally surprising. The active compounds according to the invention thus represent an enrichment of the art.

The invention also provides a process for the preparation of a 1-azolyl-4-hydroxy-butane derivative of the formula (I) in which a 1-bromo-4-(R-oxy)butan-2-one of the general formula

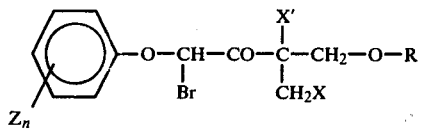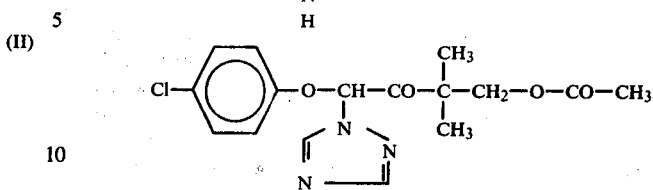 (II)

in which
R, X, X¹, Z and n have the abovementioned meanings, is reacted with an azole of the general formula

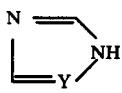 (III), in which
Y has the abovementioned meaning, in the presence of a diluent and of an acid-binding agent and, if appropriate, the azolyl-ketone thereby obtained is selectively reduced, in a manner which is in itself known, by means of a complex borohydride, if appropriate in the presence of a diluent.

In some cases it has proved advantageous to "transesterify" individual compounds, starting from the 4-acetoxy-1-azolyl-1-phenoxy-butan-2-ones obtainable according to the invention, via the corresponding 1-azolyl-4-hydroxy-1-phenoxy-butan-2-ones. For this purpose, the 4-acetoxy-1-azolyl-1-phenoxy-butan-2-ones are first subjected to hydrolytic scission with concentrated hydrochloric acid in the presence of a diluent. The 1-azolyl-4-hydroxy-1-phenoxybutan-2-ones thereby produced are then subsequently reacted, if appropriate, with acid chlorides, isocyanates or sulphonyl chlorides in a generally known manner, as shown in the preparative examples hereinbelow.

If 4-acetoxy-1-bromo-1-(4-chlorophenoxy)-3,3-dimethyl-butan-2-one and 1,2,4-triazole are used as starting materials, the course of the reaction can be represented by the following equation:

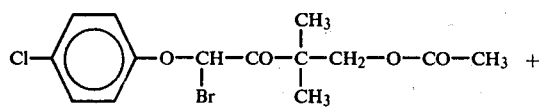

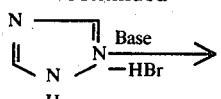

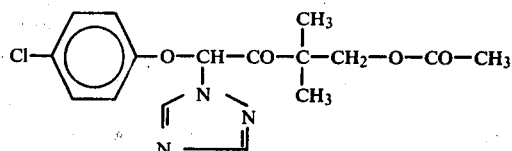

If 4-acetoxy-1-(4-chlorophenoxy)-3,3-dimethyl-1-(1,2,4-triazol-1-yl)butan-2-one and sodium borohydride are used as starting materials, the course of the reaction can be represented by the following equation:

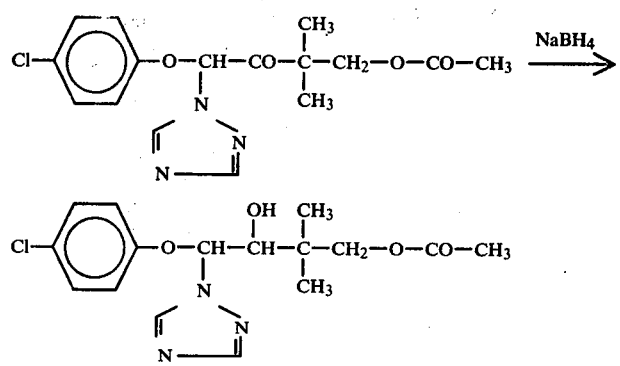

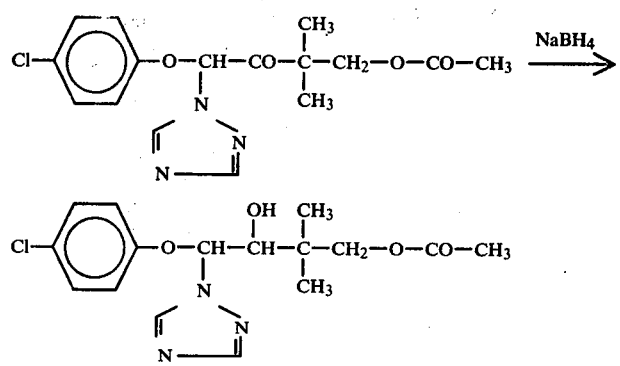

The following may be mentioned as examples of starting materials of the formula (II): 4-acetoxy-1-bromo-1-(2,4-dichlorophenoxy)-3,3-dimethyl-butan-2-one, 4-acetoxy-1-bromo-1-(4-chlorophenoxy)-3,3-dimethyl-butan-2-one, 4-acetoxy-1-bromo-1-(4-fluorophenoxy)-3,3-dimethyl-butan-2-one, 4-acetoxy-1-bromo-1-(4-bromophenoxy)-3,3-dimethyl-butan-2-one, 4-acetoxy-1-bromo-1-(2,4,5-trichlorophenoxy)-3,3-dimethyl-butan-2-one, 4-acetoxy-1-bromo-1-(2-methylphenoxy)-3,3-dimethyl-butan-2-one, 4-acetoxy-1-bromo-1-(3,4-dimethylphenoxy)-3,3-dimethyl-butan-2-one, 4-acetoxy-1-bromo-1-(4-chloro-3,5-dimethylphenoxy)-3,3-dimethyl-butan-2-one, 4-acetoxy-1-bromo-1-(2-methyl-5-nitro-phenoxy)-3,3-dimethyl-butan-2-one, 4-acetoxy-1-bromo-1-(2-cyclohexylphenoxy)-3,3-dimethyl-butan-2-one, 4-acetoxy-1-bromo-1-(4-methoxyphenoxy)-3,3-dimethyl-butan-2-one, 4-acetoxy-1-bromo-1-(3-trifluoromethylphenoxy)-3,3-dimethyl-butan-2-one, 4-acetoxy-1-bromo-1-(2-phenylphenoxy)-3,3-dimethyl-butan-2-one, 4-acetoxy-1-bromo-1-[4-(4'-chlorophenoxy)-phenoxy]-3,3-dimethyl-butan-2-one, 4-acetoxy-1-bromo-1-[4-(4'-chlorobenzyl)-phenoxy]-3,3-dimethyl-butan-2-one, 4-acetoxy-1-bromo-1-(4-cyanophenoxy)-3,3-dimethyl-butan-2-one, 4-acetoxy-1-bromo-1-(4-nitrophenoxy)-3,3-dimethyl-butan-2-one, 4-acetoxy-1-bromo-1-(4-biphenylyloxy)-3,3-dimethyl-butan-2-one, 4-acetoxy-1-bromo-1-[4(4'-chlorophenyl)-phenoxy]-3,3-dimethyl-butan-2-one, 1-bromo-1-(4-chlorophenoxy)-4-trimethylacetoxy-3,3-dimethyl-butan-2one, 1-bromo-1-(4-chlorophenoxy)-4-propionyloxy-3,3-dimethylbutan-2-one, 1-bromo-1-(4-chlorophenoxy)-4-vinylcarbonyl-oxy-3,3-dimethyl-butan-2-one, 1-bromo-1-(4-chlorophenoxy)-4-chloroacetoxy-3,3-dimethyl-butan-2-one, 1-bromo-1-(4-chlorophenoxy)-4-methylcarbamoyloxy-3,3-dimethyl-butan-2-one, 1-bromo-1-(4-chlorophenoxy)-4-dimethylcarbamoyloxy-3,3-dimethyl-butan-2-one, 1-bromo-1-(4-chlorophenoxy)-4-phenylcarbamoyloxy-3,3-dimethyl-butan-2-one, 1-bromo-1-(4-chlorophenoxy)-4-(α-chloropropionyloxy)-3,3-dimethylbutan-2-one, 1-bromo-1-(4-chlorophenoxy)-4-benzoyloxy-3,3-dimethyl-butan-2-one, 1-bromo-1-(4-chlorophenoxy)-4-(4-chlorobenzoyloxy)-3,3-dimethyl-butan-2-one, 1-bromo-1-(4-chlorophenoxy)-4-(2,4-dichlorobenzoyloxy)-3,3-dimethyl-butan-2-one, 1-bromo-1-(4-chlorophenoxy)-4-phenylacetoxy-3,3-dimethyl-butan-2-one, 1-bromo-1-(4-chlorophenoxy)-4-(4-chlorophenylacetoxy)-3,3-dimethyl-butan-2-one, 1-bromo-1-(4-chlorophenoxy)-4-(2,4-dichlorophenylacetoxy)-3,3-dimethyl-butan-2-one, 1-bromo-1-(4-chlorophenoxy)-4-aminoacetoxy-3,3-dimethyl-butan-2-one, 1-bromo-1-(4-chlorophenoxy)-4-phenoxyacetoxy-3,3-dimethyl-butan-2-one, 1-bromo-1-(4-chlorophenoxy)-4-(4-chlorophenoxyacetoxy)-3,3-dimethyl-butan-2-one, 1-bromo-1-(4-chlorophenoxy)-4-(2,4-dichlorophenoxyacetoxy)-3,3-dimethyl-butan-2-one, 1-bromo-1-(4-chlorophenoxy)-4-cyanoacetoxy-3,3-dimethyl-butan-2-one, 1-bromo-1-(4-chlorophenoxy)-4-methoxyacetoxy-3,3-dimethylbutan-2-one, 1-bromo-1-(4-chlorophenoxy)-4-methoxycarbonylacetoxy-3,3-dimethyl-butan-2-one, 1-bromo-1-(2,4-dichlorophenoxy)-4-trimethylacetoxy-3,3-dimethyl-butan-2-one, 1-bromo-1-(2,4-dichlorophenoxy)-4-propionyloxy-3,3-dimethyl-butan-2-one, 1-bromo-1-(2,4-dichlorophenoxy)-4-vinylcarbonyloxy-3,3-dimethyl-butan-2-one, 1-bromo-1-(2,4-dichlorophenoxy)-4-chloroacetoxy-3,3-dimethyl-butan-2-one, 1-bromo-(2,4-dichlorophenoxy)-4-methylcarbamoyloxy-3,3-dimethyl-butan-2-one, 1-bromo-1-(2,4-dichlorophenoxy)-4-dimethylcarbamoyloxy-3,3-dimethyl-butan-2-one, 1-bromo-1-(2,4-dichlorophenoxy)-4-phenylcarbamoyloxy-3,3-dimethyl-butan-2-one, 1-bromo-1-(2,4-dichlorophenoxy)-4-(α-chloropropionyloxy)-3,3-dimethyl-butan-2-one, 1-bromo-1-(2,4-dichlorophenoxy)4-benzoyloxy-3,3-dimethyl-butan-2-one, 1-bromo-1-(2,4-dichlorophenoxy)-4-(4-chlorobenzoyloxy)-3,3-dimethyl-butan-2-one, 1-bromo-1-(2,4-dichlorophenoxy)-4-(2,4-dichlorobenzoyloxy)-3,3-dimethyl-butan-2-one, 1-bromo-1-(2,4-dichlorophenoxy)-4-phenylacetoxy-3,3-dimethyl-butan-2-one, 1-bromo-1-(2,4-dichlorophenoxy)-4-(4-chlorophenylacetoxy)-3,3-dimethyl-butan-2-one, 1-bromo-1-(2,4-dichlorophenoxy)-4-(2,4-dichlorophenylacetoxy)-3,3-dimethylbutan-2-one, 1-bromo-(2,4-dichlorophenoxy)-4-aminoacetoxy-3,3-dimethyl-butan-2-one, 1-bromo-1-(2,4-dichlorophenoxy)-4-phenoxyacetoxy-3,3-dimethyl-butan-2-one, 1-bromo-1-(2,4-dichlorophenoxy)-4-(4-chlorophenoxyacetoxy)-3,3-dimethyl-butan-2-one, 1-bromo-1-(2,4-dichlorophenoxy)-4-(2,4-dichlorophenoxyacetoxy)-3,3-dimethyl-butan-2-one, 1-bromo-1-(2,4-dichlorophenoxy)-4-cyano-acetoxy-3,3-dimethylbutan-2-one, 1-bromo-1-(2,4-dichlorophenoxy)-4-methoxyacetoxy-3,3-dimethyl-butan-2-one and 1-bromo-1-(2,4-dichlorophenoxy)-4-methoxycarbonylacetoxy-3,3-dimethyl-butan-2-one.

The 1-bromo-4-(R-oxy)-butan-2-ones of the formula (II) to be used as starting materials have not previously been described in the literature, but can be prepared in accordance with known processes by, for example, reacting known phenols of the general formula

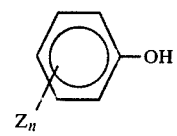

in which
Z and n have the abovementioned meanings, with a bromoketone of the general formula

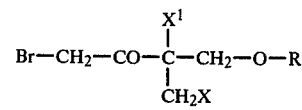

in which
R, X and $X^1$ have the abovementioned meanings. The active hydrogen atom which still remains is subsequently replaced by bromine in the usual manner, as shown in preparative examples hereinbelow.

The bromoketones of the formula (V) are generally known compounds of organic chemistry. They are obtained by reacting known ketones of the general formula

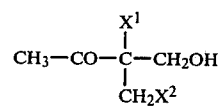

in which
$X^1$ has the abovementioned meaning and
$X^2$ represents hydrogen or hydroxyl, if appropriate, with acid chlorides, acid anhydrides, isocyanates or sulphonyl chlorides, in a generally known manner. The active hydrogen atom which still remains is then replaced by bromine in the usual manner.

The azoles of the formula (III) are well known compounds in organic chemistry.

Preferred diluents for the reaction according to the invention are inert organic solvents, especially ketones, such as diethyl ketone, and especially acetone and methyl ethyl ketone; nitriles, such as propionitrile and especially acetonitrile; alcohols, such as ethanol or isopropanol; ethers, such as tetrahydrofuran or dioxane; benzene; formamides, such as, in particular, dimethylformamide; and halogenated hydrocarbons, such as methylene chloride, carbon tetrachloride or chlorform.

The reaction is carried out in the presence of an acid-binding agent. All inorganic or organic acid-binding agents which can usually be employed may be added, such as alkali metal carbonates, for example sodium carbonate, potassium carbonate and sodium bicarbonate, or such as tertiary lower alkylamines, cycloalkylamines or aralkylamines, for example triethylamine, N,N-dimethylcyclohexylamine, dicyclohexylmethylamine, N,N-dimethylbenzylamine and also pyridine and diazabicyclo-octane. However, an appropriate excess of the azole (III) can also be used.

The reaction temperatures can be varied within a substantial range. In general, the reaction is carried out at from 20° to 150° C., preferably at from 60° to 120° C. If a solvent is present, the reaction is advantageously carried out at the boiling point of the particular solvent.

In carrying out the process according to the invention, preferably 1 to 2 moles of the azole and 1 to 2 moles of acid-binding agent are employed per mole of the compounds of the formula (II). To isolate the compounds of the formula (I), the solvent is distilled off, the residue is taken up in an organic solvent and the solution is washed with water. The organic phase is dried over sodium sulphate and freed from the solvent in vacuo. The residue is purified by distillation or recrystallization.

For the selective reduction, polar organic solvents can be used as diluents for the reaction according to the invention, especially alcohols, such as methanol, ethanol, butanol and isopropanol, and ethers, such as diethyl ether or tetrahydrofuran. The reaction is in general carried out at from 0° to 30° C., preferably at 0° to 20° C. For this reaction, about 1 mole of a borohydride, such as sodium borohydride or lithium borohydride, is employed per mole of the compound of the formula (II). To isolate the compounds of the formula (I), the residue is taken up in, for example, dilute hydrochloric acid and the solution is then rendered alkaline and extracted with an organic solvent, or the residue is only mixed with water and the mixture is extracted by shaking with an organic solvent. The further working up is carried out in the usual manner.

The following may be mentioned as examples of particularly active compounds according to the invention: 4-acetoxy-1-(2-cyclohexylphenoxy)-3,3-dimethyl-1-(1,2,4-triazol-1-yl)-butan-2-one and -ol, 4-acetoxy-1-(2-cyclohexylphenoxy)-3,3-dimethyl-1-(imidazol-1-yl)-butan-2-one and -ol, 4-chloroacetoxy-1-(4-chlorophenoxy)-3,3-dimethyl-1-(1,2,4-triazol-1-yl)-butan-2-one and -ol, 4-chloroacetoxy-1-(4-chlorophenoxy)-3,3-dimethyl-1-(imidazol-1-yl)-butan-2-one and -ol, 1-[4-(4'-chlorophenyl)-phenoxy]-3,3-dimethyl-4-methylcarbamoyloxy-1-(1,2,4-triazol-1-yl)-butan-2-one and -ol, 1-[4-(4'-chlorophenyl)-phenoxy]-3,3-dimethyl-1-(imidazol-1-yl)-4-methylcarbamoyloxy-butan-2-one and -ol, 1-(4-chlorophenoxy)-3,3-dimethyl-4-hydroxy-1-(1,2,4-triazol-1-yl)-butan-2-one and -ol, 1-(4-chlorophenoxy)-3,3-dimethyl-4-hydroxy-1-(imidazol-1-yl)-butan-2-one and -ol, 4-acetoxy-1-(4-chlorophenoxy)-3,3-dimethyl-1-(1,2,4-triazol-1-yl)-butan-2-ol, 4-acetoxy-1-(4-chlorophenoxy)-3,3-dimethyl-1-(imidazol-1-yl)-butan-2-ol, 1-(4-chlorophenoxy)-3,3-dimethyl-4-phenylcarbamoyloxy-1-(1,2,4-triazol-1-yl)-butan-2-one and -ol, 1-(4-chlorophenoxy)-3,3-dimethyl-1-(imidazol-1-yl)-4-phenylcarbamoyloxy-butan-2-one and -ol, 1-(4-chlorophenoxy)-3,3-dimethyl-4-(hexa-2,4-dienylcarbonyloxy)-1-(1,2,4-triazol-1-yl)-butan-2-one and -ol, 1-(4-chlorophenoxy)-3,3-dimethyl-4-(hexa-2,4-dienyl-carbonyloxy)-1-(imidazol-1-yl)-butan-2-one and -ol, 4-ethylcarbonyloxy-1-(4-chlorophenoxy)-3,3-dimethyl-1-(1,2,4-triazol-1-yl)-butan-2-one and -ol, 4-ethylcarbonyloxy-1-(4-chlorophenoxy)-3,3-dimethyl-1-(imidazol-1-yl)-butan-2-one and -ol, 4-ethylcarbonyloxy-1-[4-(4'-chlorophenyl)-phenoxy]-3,3-dimethyl-1-(imidazol-1-yl)-butan-2-one and -ol, 1-(4-chlorophenoxy)-3,3-dimethyl-4-propylcarbonyloxy-1-(1,2,4-triazol-1-yl)-butan-2-one and -ol, 1-(4-chlorophenoxy)-3,3-dimethyl-4-iso-propylcarbonyloxy-1-(1,2,4-triazol-1-yl)-butan-2-one and -ol, 1-(4-chlorophenoxy)-3,3-dimethyl-4-iso-propylcarbonyloxy-1-(imidazol-1-yl)-butan-2-one and -ol, 1-(4-chlorophenoxy)-3,3-dimethyl-4-pentylcarbonyloxy-1-(1,2,4-triazol-1-yl)-butan-2-one and -ol, 1-[4-(4'-chlorophenyl)-phenoxy]-3,3-dimethyl-1-(imidazol-1-yl)-4-pentylcarbonyloxy-butan-2-one and -ol, 1-(4-chlorophenoxy)-3,3-dimethyl-4-heptylcarbonyloxy-1-(1,2,4-triazol-1-yl)-butan-2-one and -ol, 1-[4-(4'-chlorophenyl)-phenoxy]-3,3-dimethyl-4-heptylcarbonyloxy-1-(imidazol-1-yl)-butan-2-one and -ol, 1-(4-chlorophenoxy)-3,3-dimethyl-4-nonylcarbonyloxy-1-(1,2,4-triazol-1-yl)-butan-2-one and -ol, 1-(4-chlorophenoxy)-3,3-dimethyl-1-(imidazol-1-yl)-4-nonylcarbonyloxy-butan-2-one and -ol, 1-(4-chlorophenoxy)-3,3-dimethyl-1-(1,2,4-triazol-1-yl)-4-undecanylcarbonyloxy-butan-2-one and -ol, 1-(4-chlorophenoxy)-3,3-dimethyl-1-(1,2,4-triazol-1-yl)-4-tridecanylcarbonyloxy-butan-2-one and -ol, 1-[4-(4'-chlorophenyl)-phenoxy]-3,3-dimethyl-1-(imidazol-1-yl)-4-tridecanylcarbonyloxy-butan-2-one and -ol, 1-(4-chlorophenoxy)-3,3-dimethyl-4-heptadecanylcarbonyloxy-1-(1,2,4-triazol-1-yl)-butan-2-one and -ol, 1-(4-chlorophenoxy)-3,3-dimethyl-4-pivaloyloxy-1-(1,2,4-triazol-1-yl)-butan-2-one and -ol, 1-(4-chlorophenoxy)-3,3-dimethyl-1-(imidazol-1-yl)-4-pivaloyloxy-butan-2-one and -ol, 1-[4-(4'-chlorophenyl)-phenoxy]-3,3-dimethyl-1-(imidazol-1-yl)-4-pivaloyloxy-butan-2-ol, 4-benzoyloxy-1-(4-chlorophenoxy)-3,3-dimethyl-1-(1,2,4-triazol-1-yl)-butan-2-one and -ol, 4-(4-chlorobenzoyloxy)-1-(4-chlorophenoxy)-3,3-dimethyl-1-(1,2,4-triazol-1-yl)-butan-2-one and -ol, 4-(4-chlorobenzoyloxy)-1-(4-chlorophenoxy)-3,3-dimethyl-1-(imidazol-1-yl)-butan-2-one and -ol, 4-(4-chlorobenzoyloxy)-1-[4-(4'-chlorophenyl)-phenoxy]-3,3-dimethyl-1-(imidazol-1-yl)-butan-2-one and -ol, 4-benzyl-carbonyloxy-1-(4-chlorophenoxy)-3,3-dimethyl-1-(1,2,4-triazol-1-yl)-butan-2-one and -ol, 1-(4-chlorophenoxy)-4-cyclohexyl-carbonyloxy-3,3-dimethyl-1-(1,2,4-triazol-1-yl)-butan-2-one and -ol, 4-chloroacetoxy-1-(4-chlorophenoxy)-3,3-dimethyl-1-(1,2,4-triazol-1-yl)-butan-2-one and -ol, 4-chloroacetoxy-1-(4-chlorophenoxy)-3,3-dimethyl-1-(imidazol-1-yl)-butan-2-one and -ol, 4-chloroacetoxy-1-[4-(4'-chlorophenyl)-phenoxy]-3,3-dimethyl-1-(imidazol-1-yl)-butan-2-one and -ol, 1-(4-chlorophenoxy)-4-dichloroacetoxy-3,3-dimethyl-1-(1,2,4-triazol-1-yl)-butan-2-one and -ol, 1-(4-chlorophenoxy)-4-dichloroacetoxy-3,3-dimethyl-1-(imidazol-1-yl)-butan-2-one and -ol, 4-(2-chloroethylcarbonyloxy)-1-(4-chlorophenoxy)-3,3-dimethyl-1-(1,2,4-triazol-1-yl)-butan-2-one and -ol, 1-(4-chlorophenoxy)-4-(3-chloropropylcarbonyloxy)-3,3-dimethyl-1-(1,2,4-triazol-1-yl)-butan-2-one and -ol, 1-(4-chlorophenoxy)-3,3-dimethyl-4-(1-methylvinylcarbonyloxy)-1-(1,2,4-triazol-1-yl)-butan-2-one and -ol, 1-(4-chlorophenoxy)-3,3-dimethyl-1-(imidazol-1-yl)-4-(1-methylvinylcarbonyloxy)-butan-2-one and -ol, 1-[4-(4'-chlorophenyl)-phenoxy]-3,3-dimethyl-1-(imidazol-1-yl)-4-(1-methylvinylcarbonyloxy)-butan-2-one and -ol, 1-(4-chlorophenoxy)-3,3-dimethyl-4-(penta-1,3-dienylcarbonyloxy)-1-(1,2,4-triazol-1-yl)-butan-2-one and -ol, 1-(4-chlorophenoxy)-4-cyanoacetoxy-3,3-dimethyl-1-(1,2,4-triazol-1-yl)-butan-2-one and -ol, 1-[4-(4'-chlorophenyl)-phenoxy]-4-cyanoacetoxy-3,3-dimethyl-1-(imidazol-1-yl)-butan-2-one and -ol, 4-ethoxycarbonylmethylcarbonyloxy-1-(4-chlorophenoxy)-3,3-dimethyl-1-(1,2,4-triazol-1-yl)-butan-2-one and -ol, 4-ethoxymethylcarbonyloxy-1-(4-chlorophenoxy)-3,3-dimethyl-1-(1,2,4-triazol-1-yl)-butan-2-one and -ol, 4-ethoxymethylcarbonyloxy-1-[4-(4'-chlorophenyl)-phenoxy]-3,3-dimethyl-1-(imidazol-1-yl)-butan-2-one and -ol, 1-(4-chlorophenoxy)-4-(2,4-dichlorophenoxymethylcarbonyloxy)-3,3-dimethyl-1-(1,2,4-triazol-1-yl)-butan-2-one and -ol, 1-(4-chlorophenoxy)-4-(2,4-dichlorophenoxymethylcarbonyloxy)-3,3-dimethyl-1-(imidazol-1-yl)-butan-2-one and -ol, 1-[4-(4'-chlorophenyl)-phenoxy]-4-(2,4-dichlorophenoxymethylcarbonyloxy)-3,3-dimethyl-1-(imidazol-1-yl)- butan-2-one and -ol, 4-acetylaminomethylcarbonyloxy-1-(4-chlorophenoxy)-3,3-dimethyl-1-(1,2,4-triazol-1-yl)-butan-2-one and -ol, 4-acetylaminomethylcarbonyloxy-1-[4-(4'-chlorophenyl)-phenoxy]-3,3-dimethyl-1-(imidazol-1-yl)-butan-2-one and -ol, 1-(4-chlorophenoxy)-3,3-dimethyl-4-methylsulphonyl-oxy-1-(1,2,4-triazol-1-yl)-butan-2-one and -ol, 1-(4-chlorophenoxy)-3,3-dimethyl-1-(imidazol-1-yl)-4-methylsulphonyloxy-butan-2-one and -ol, 1-[4-(4'-chlorophenyl)-phenoxy]-3,3-dimethyl-1-(imidazol-1-yl)-4-methylsulphonyloxy-butan-2-one and -ol, 1-(4-chlorophenoxy)-3,3-dimethyl-4-hexadecanylcarbonyloxy-1-(1,2,4-triazol-1-yl)-butan-2-one and -ol, 4-butylcarbonyloxy-1-(4-chlorophenoxy)-3,3-dimethyl-1-(1,2,4-triazol-1-yl)-butan-2-one and -ol, 4-(ethyl-methyl-acetoxy)-1-(4-chlorophenoxy)-3,3-dimethyl-1-(1,2,4-triazol-1-yl)-butan-2-one and -ol, 1-(4-chlorophenoxy)-4-iso-butylcarbonyloxy-3,3-dimethyl-1-(1,2,4-triazol-1-yl)-butan-2-one and -ol, 1-(4-chlorophenoxy)-3,3-dimethyl-4-methylcarbamoyloxy-1-(1,2,4-triazol-1-yl)-butan-2-one and -ol, 1-(4-chlorophenoxy)-3,3-dimethyl-1-(imidazol-1-yl)-4-methylcarbamoyloxy-butan-2-one and -ol, 1-(4-chlorophenoxy)-3,3-dimethyl-4-phenylcarbamoyloxy-1-(1,2,4-triazol-1-yl)-butan-2-one and -ol, 1-[4-(4'-chlorophenyl)-phenoxy]-3,3-dimethyl-1-(imidazol-1-yl)-4-phenylcarbamoyloxy-butan-2-one and -ol, 4-ethylcarbamoyloxy-1-(4-chlorophenoxy)-3,3-dimethyl-1-(1,2,4-triazol-1-yl)-butan-2-one and -ol, 4-acetoxy-3-ethyl-1-(4-chlorophenoxy)-3-methyl-1-(1,2,4-triazol-1-yl)-butan-2-one and -ol, 4-acetoxy-1-(4-chlorophenoxy)-3-(4-chlorophenyl)-3-methyl-1-(1,2,4-triazol-1-yl)-butan-2-one and -ol and 4-acetoxy-3-acetoxymethyl-1-(4-chlorophenoxy)-3-(4-chlorophenyl)-1-(1,2,4-triazol-1-yl)-butan-2-one and -ol.

The active compounds according to the invention exhibit a powerful fungitoxic action and a bacteriotoxic action. They do not damage crop plants in the concentrations required for combating fungi and bacteria. For these reasons they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi and bacteria which attack above-ground parts of plants or attack the plants through the soil, and also against seed-borne pathogens.

They display a particularly good activity against parasitic fungi on above-ground parts of plants, such as species of Erysiphe, species of Podosphaera and species of Venturia and also against species of Pyricularia and species of Pellicularia. Good actions are achieved against the pathogen of apple scab (Fusicladium dendriticum). Furthermore, the compounds exhibit a high activity against cereal diseases, such as powdery mildew of cereals and powdery midlew of barley. An aspect to be singled out is that the active compounds according to the invention not only display a protective action but are also systemically active. Thus it proves possible to protect plants against fungal attack by supplying the active compound to the above-ground parts of the plant through the soil and the root or through the seed.

As plant protection agents, the compounds according to the invention can be used for the treatment of soil, for the treatment of seed and for the treatment of above-ground parts of plants.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as dichlorodifluoromethane and trichlorofluoromethane; inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselgur, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl ar polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and bactericides, or insecticides, acaricides, nematocides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the active compound concentrations in the use forms can be varied within a substantial range. They are, in general, from 0.1 to 0.0001 percent by weight, preferably from 0.05 to 0.0001 percent.

In the treatment of seed, amounts of active compound of 0.001 to 50 g per kilogram of seed, preferably 0.01 to 10 g, are generally employed.

For the treatment of soil, amounts of active compound of 1 to 1,000 g per cubic meter of soil, preferably 10 to 200 g, are generally employed.

Furthermore, the present invention contemplates methods of selectively killing, combating or controlling pests, e.g. fungi and bacteria, which comprises applying to at least one of correspondingly (a) such fungi, (b) such bacteria, and (c) the corresponding habitat thereof, i.e. the locus to be protected, e.g. to a growing crop, to an area where a crop is to be grown or to a domestic animal, a correspondingly combative or toxic amount, i.e. fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1 a) Preparation of the starting material

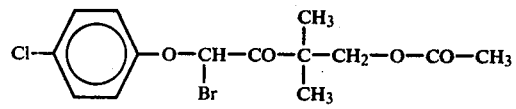

170 g (0.72 mol) of 4-acetoxy-1-bromo-3,3-dimethyl-butan-2-one in 200 ml of acetone were added dropwise, over the course of 100 minutes, to a suspension of 92.1 g (0.72 mol) of 4-chlorophenol and 108 g (0.72 mol) of potassium carbonate in 1,000 ml of acetone. After heating for 15 hours whilst stirring under reflux, the mixture was filtered and the filtrate was concentrated by distilling off the solvent in vacuo. The residue was taken up in 200 ml of methylene chloride and the solution was washed three times with 50 ml of water at a time, dried over sodium sulphate and concentrated. The oily residue was distilled. 153 g (72% of theory) of 4-acetoxy-1-(4-chlorophenoxy)-3,3-dimethyl-butan-2-one of boiling point 140°–145° C./0.2 mm Hg was obtained.

56.9 g (0.2 mol) of 4-acetoxy-1-(4-chlorophenoxy)-3,3-dimethyl-butan-2-one were dissolved in 350 ml of carbon tetrachloride. 10.3 g (0.2 mol) of bromine were added dropwise, at room temperature, in such a way that the bromine was steadily consumed. Thereafter, the mixture was stirred for 30 minutes at room temperature. After distilling off the solvent in vacuo, 4-acetoxy-1-bromo-1-(4-chlorophenoxy)-3,3-dimethyl-butan-2-one was obtained quantitatively and could be directly reacted further.

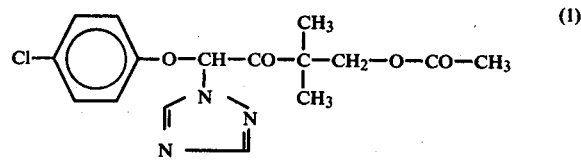

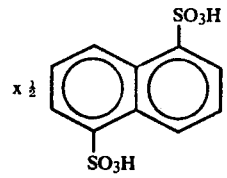

A solution of 36.3 g (0.2 mol) of crude 4-acetoxy-1-bromo-1-(4-chlorophenoxy)-3,3-dimethyl-butan-2-one in 50 ml of acetone was added dropwise, at the boil, to a suspension of 21 g (0.3 mol) of 1,2,4-triazole and 30g (0.2 mol) of potassium carbonate in 200 ml of acetone. After heating for 15 hours under reflux, the mixture was filtered and the filtrate was concentrated by distilling off the solvent in vacuo. The residue was taken up in 200 ml of methylene chloride and the solution was washed three times with 50 ml of water at a time, dried over sodium sulphate and concentrated. The residue was dissolved in 100 ml of acetone and 36 g (0.1 mol) of 1,5-naphthalenedisulphonic acid octahydrate in 100 ml of acetone were added. The crystalline precipitate which resulted was filtered off and dried. 45 g (45% of theory) of 4-acetoxy-1-(4-chloro-phenoxy)-3,3-dimethyl-1-(1,2,4-triazol-1-yl)-butan-2-one 1,5-naphthalenedisulphonate of melting point 155°–160° C. were obtained.

EXAMPLE 2

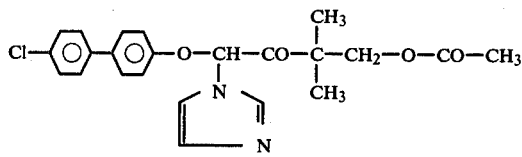 (2)

22 g (0.05 mol) of 4-acetoxy-1-bromo-1-[4-(4'-chlorophenyl)-phenoxy]-3,3dimethyl-butan-2-one were dissolved in 20 ml of acetone and the solution was added dropwise, at the boil, to 5.5 g (0.08 mol) of imidazole and 7.5 g (0.05 mol) of potassium carbonate in 80 ml of acetone. After heating for 15 hours under reflux, the mixture was filtered and the filtrate was concentrated by distilling off the solvent in vacuo. The oil which remained was washed with 50 ml of water and was crystallized, or recrystallized, from ether. 9 g (42.2% of theory) of 4-acetoxy-1-[4-(4'-chlorophenyl)-phenoxy]-3,3-dimethyl-1-(imidazol-1-yl)-butan-2-one of melting point 110°–112° C. were obtained.

EXAMPLE 3

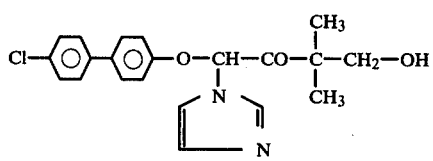 (3)

12 ml of concentrated hydrochloric acid were added to 42.8 g. (0.1 mol) of 4-acetoxy-1-[4-(4'-chlorophenyl)-phenoxy]-3,3-dimethyl-1-(imidazol-1-yl)-butan-2-one (see Example 2) in 200 ml of methanol and the mixture was heated for 8 hours under reflux. The solvent was then distilled off in vacuo and 50 ml of saturated sodium bicarbonate solution and 50 ml of pentane were added to the residue. After 2 hours, the crystalline product was filtered off. 38.9 g (100% of theory) of 1-[4-(4'-chlorophenyl)-phenoxy]-3,3-dimethyl-4-hydroxy-1-(imidazol-1-yl)-butan-2-one of melting point 133°–135° C. were obtained.

EXAMPLE 4

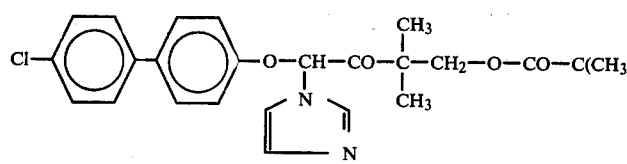 (4)

7.72 g (0.02 mol) of 1-[4-(4'-chlorophenyl)-phenoxy]-3,3-dimethyl-4-hydroxy-1-(imidazol-1-yl)-butan-2-one (see Example 3) were dissolved in 50 ml of methylene chloride, 5 ml of pivalic acid chloride were added and the mixture was heated for 5 hours under reflux. The solvent was then distilled off in vacuo, the residue was taken up in methylene chloride and the solution was washed twice with 50 ml of saturated sodium bicarbonate solution at a time and was concentrated. The residue was taken up in 50 ml of pentane, whereupon it crystallized. 5.3 g (60% of theory) of 1-[4-(4'-chlorophenyl)-phenoxy]-3,3-dimethyl-1-(imidazol-1-yl)-4-pivaloyloxy-butan-2-one of melting point 98°–103° C. were obtained.

The following compounds of the general formula

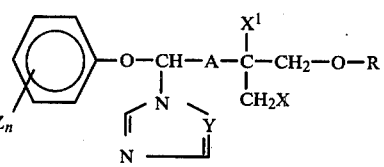 (I)

were obtained analogously to the abovementioned compounds:

Table 1

| Compound No. | $Z_n$ | Y | A | X | $X^1$ | R | Melting Point (° C.) |
|---|---|---|---|---|---|---|---|
| 5 | 4-NO$_2$ | N | CO | H | CH$_3$ | —CO—CH$_3$ | 110–111 |
| 6 | 4-(phenyl) | N | CO | H | CH$_3$ | —CO—CH$_3$ | 113–114 |
| 7 | 4-(4-Cl-phenyl) | N | CO | H | CH$_3$ | —CO—CH$_3$ | 114–115 |
| 8 | 2,4-Cl$_2$ | N | CO | H | CH$_3$ | —CO—CH$_3$ | viscous oil |
| 9 | 2,4-Cl$_2$ | N | CO | H | CH$_3$ | —CO—CH$_3$ | 173–174 |

Table 1-continued

| Compound No. | $Z_n$ | Y | A | X | $X^1$ | R | Melting Point (°C.) |
|---|---|---|---|---|---|---|---|
| | | | | | | (x ½) naphthalene-1,5-disulfonic acid | |
| 10 | — | N | CO | H | $CH_3$ | $-CO-CH_3$ | viscous oil |
| 11 | 4-Cl | N | CO | $-O-CO-CH_3$ | $CH_3$ | $-CO-CH_3$ | 85–86 |
| 12 | 4-$NO_2$ | CH | CO | H | $CH_3$ | $-CO-CH_3$ | 148–151 |
| 13 | 2,4-$Cl_2$ | CH | CO | H | $CH_3$ | $-CO-CH_3$ | 69–70 |
| 14 | 4-Cl | CH | CO | H | $CH_3$ | $-CO-CH_3$ | 72–74 |
| 15 | — | CH | CO | H | $CH_3$ | $-CO-CH_3$ | viscous oil |
| 16 | 4-(C$_6$H$_4$)-Cl | CH | CO | H | $CH_3$ | $-CO-(CH_2)_{16}-CH_3$ | 58–68 |
| 17 | 4-Cl | CH | CO | H | $CH_3$ | H | 104–105 |
| 18 | 4-Cl | N | CO | H | $CH_3$ | H | 110–111 |
| 19 | 4-(C$_6$H$_4$)-Cl | CH | CHOH | H | $CH_3$ | H | 138–143 |
| 20 | 4-Cl | CH | CO | H | $CH_3$ | $-CO-CHCl_2$ | 102–104 |
| 21 | 4-Cl | N | CHOH | H | $CH_3$ | H | 96–105 |
| 22 | 4-Cl | N— | CO | H | $CH_3$ | $-CO-C_{11}H_{23}$ | viscous oil |
| 23 | 4-Cl | N | CO | H | $CH_3$ | $-CO-CH_2Cl$ | 69 |
| 24 | 2,4-$Cl_2$ | N | CO | H | $CH_3$ | H | 104–110 |
| 25 | 4-Cl | N | CO | H | $CH_3$ | $-CO-C_5H_{11}$ | viscous oil |
| 26 | 4-(C$_6$H$_4$)-Cl | CH | CO | H | $CH_3$ | $-CO-C_7H_{15}$ | 50–53 |
| 27 | 4-Cl | N | CO | H | $CH_3$ | $-CO-C_2H_5$ | 58–60 |
| 28 | 4-Cl | N | CO | H | $CH_3$ | $-CO-CHCl_2$ | 60–62 |
| 29 | 4-Cl | N | CO | H | $CH_3$ | $-CO-C_{17}H_{35}$ | 26 |
| 30 | 4-Cl | N | CO | H | $CH_3$ | $-CO-(CH_2)_2-CH_2Cl$ | 56–58 |

Table 1-continued

| Compound No. | $Z_n$ | Y | A | X | $X^1$ | R | Melting Point (° C.) |
|---|---|---|---|---|---|---|---|
| 31 | 4-Cl | | N | CO | H | $CH_3$ | 73 |
| | | | | | | —CO—⟨phenyl-H⟩ | |
| 32 | 4-Cl | | N | CO | H | $CH_3$ | 85 |
| | | | | | | —CO—$CH_2$—⟨phenyl⟩ | |
| 33 | 4-⟨phenyl-Cl⟩ | | CH | CO | H | $CH_3$ | 72–75 |
| | | | | | | —CO—$C_9H_{19}$ | |

The fungicidal and bactericidal activity of the compounds of this invention is illustrated by the following biotest examples wherein the active compounds according to the present invention are each identified by the number given hereinabove and the known comparison compounds are identified as follows:

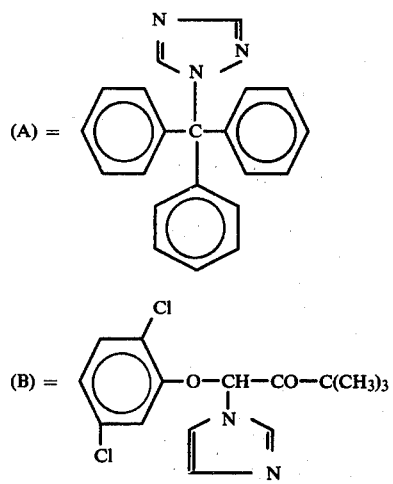

EXAMPLE 5

Shoot treatment test/powdery mildew and cereals/-protective (leaf-destructive mycosis)

To produce a suitable preparation of active compound, 0.25 g part by weight of active compound was taken up in 25 parts by weight of dimethylformamide and 0.06 part by weight of alkylaryl polyglycol ether; then 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of Erysiphe graminis var. hordei.

After 6 days' dwell time of the plants at a temperature of 21°–22° C. and 80–90% atmospheric humidity the occurrence of mildew pustules of the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and the degrees of infection can be seen from the table which follows:

Table 2

| | Shoot treatment test/powdery mildew of cereals/protective | |
|---|---|---|
| Active compounds | Active compound concentration in the spray liquor in % by weight | Infection in % of the untreated control |
| untreated | — | 100.0 |
| (A) | 0.025 | 100.0 |
| (1) | 0.025 | 0.0 |
| (5) | 0.025 | 50.0 |
| (6) | 0.025 | 50.0 |
| (7) | 0.025 | 32.5 |
| (8) | 0.025 | 0.0 |
| (10) | 0.025 | 0.0 |
| (11) | 0.025 | 16.3 |
| (12) | 0.025 | 0.0 |
| (13) | 0.025 | 50.0 |
| (14) | 0.025 | 13.8 |
| (15) | 0.025 | 0.0 |

EXAMPLE 6

Powdery mildew of barley (Erysiphe graminis var. hordei)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of Erysiphe graminis var. hordei and grown on at 21°–22° C. and 80–90% relative atmospheric humidity and 16 hours' exposure to light. The typical mildew pustules formed on the leaves over the course of 6 days.

The degree of infection was expressed as a percentage of the infection of the untreated control plants.

Thus, 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

Table 3

Powdery mildew of barley test
(*Erysiphe graminis* var. *hordei*)/
systemic

| Active compounds | Active compound concentration in the dressing in % by weight | Amount of dressing used in g/kg of seed | Infection in % of the untreated control |
|---|---|---|---|
| without dressing | — | — | 100.0 |
| (A) | 25 | 10 | 88.8 |
| (B) | 25 | 10 | 100.0 |
| (1) | 25 | 10 | 0.0 |
| (5) | 25 | 10 | 0.0 |
| (8) | 25 | 10 | 0.0 |
| (10) | 25 | 10 | 0.0 |
| (12) | 25 | 10 | 27.5 |
| (13) | 25 | 10 | 3.8 |
| (14) | 25 | 10 | 0.0 |
| (15) | 25 | 10 | 55.0 |

EXAMPLE 7

Bacteria test/*Xanthomonas oryzae*
Solvent: 11.75 parts by weight of acetone
Dispersing agent: 0.75 part by weight of alkylaryl polyglycol ether
Water: 987.50 parts by weight The amount of active compound required for the desired active compound concentration in the spray liquor was mixed with the stated amount of the solvent and of the dispersing agent and the concentrate was diluted with the stated amount of water.

30 rice plants which were about 30 days old were sprayed with the spray liquor until dripping wet. The plants remained in a greenhouse, at temperatures of 22° to 24° C. and a relative atmospheric humidity of about 70%, until they had dried. Needles were then dipped into an aqueous bacterial suspension of *Xanthomonas oryzae* and the plants were inoculated by pricking the leaves. After the inoculation, the leaves stood for 24 hours at 100% relative atmospheric humidity and thereafter in a room at 26° to 28° C. and 80% relative atmospheric humidity.

10 days after the inoculation, the infection of all pricked inoculated leaves of plants which had beforehand been treated with the preparation was evaluated, using a scale of from 1 to 9. 1 denoted 100action, 3 denoted good action, 5 denoted moderate action and 9 denoted no action.

The active compounds, active compound concentrations and results can be seen from the table which follows:

Table 4

| Bacteria test / *xanthomonas oryzae* | |
|---|---|
| Active compound | Infection rating at an active compound concentration of 0.025% |
| untreated control | 9 |

Table 4-continued

| Bacteria test / *xanthomonas oryzae* | |
|---|---|
| Active compound | Infection rating at an active compound concentration of 0.025% |
| (12) | 5 |
| (8) | 5 |
| (11) | 3 |

It will be appreciated that the instant specification and examples are set forth by way of illustration and not limitation, and that various modifications and changes may be made without departing from the spirit and scope of the present invention.

What is claimed:

1. A 1-azolyl-4-hydroxy-1-phenoxy-butane derivative of the formula $$Z_n-\underset{}{\underset{}{\bigcirc}}-O-CH-A-\underset{CH_2X}{\overset{X'}{\underset{|}{C}}}-CH_2-O-R$$

in which
R is hydrogen, —CO-$R^1$ or —$SO_2$-$R^2$,
$R^1$ is alkyl with 1 to 18 carbon atoms optionally substituted by halogen, amino, acetylamino, alkoxy with 1 to 4 carbon atoms, or alkoxycarbonyl with 1 to 4 carbon atoms in the alkyl moiety, alkenyl or alkynyl with 2 to 6 carbon atoms, cycloalkyl with 5 to 7 carbon atoms, phenyl or phenyl-$C_{1-4}$-alkyl optionally substituted on the phenyl ring by halogen, amino, cyano, nitro or alkyl with 1 to 2 carbon atoms, alkylamino or dialkylamino with 1 to 4 carbon atoms in each alkyl moiety, or phenylamino optionally substituted by halogen, nitro or cyano,
$R^2$ is alkyl with 1 to 4 carbon atoms, or phenyl optionally substituted by halogen, amino, cyano, nitro or alkyl with 1 to 2 carbon atoms,
A is —CO— or CH(OH),
X is H or —OR,
$X^1$ is alkyl with 1 or 2 carbon atoms, or phenyl optionally substituted by halogen or by alkyl with 1 to 2 carbon atoms,
Y is CH or N,
Z is halogen, alkyl with 1 to 4 carbon atoms, cycloalkyl with 5 to 7 carbon atoms, halogenoalkyl with 1 or 2 carbon atoms and 1 to 5 halogen atoms, alkoxy or alkylthio each with 1 or 2 carbon atoms, alkoxycarbonyl with 1 to 5 carbon atoms in the alkoxy moiety, amino, cyano, nitro, phenyl or phenoxy optionally substituted by halogen, amino cyano, nitro or alkyl with 1 to 2 carbon atoms or phenyl-$C_{1-2}$-alkyl optionally substituted in the alkyl moiety with alkylcarbonyl with a total of up to 3 carbon atoms and on the phenyl ring with halogen, nitro or cyano, and
n is 0, 1, 2, 3, 4 or 5,
or a salt thereof.

2. A compound according to claim 1, in which n is 0, 1, 2 or 3, or a salt thereof with a physiologically tolerated acid.

3. A compound according to claim 1 wherein such compound is 4-acetoxy-1-(4-chloro-phenoxy)-3,3- dimethyl-1-(1,2,4-triazol-1-yl)-butan-2-one of the formula

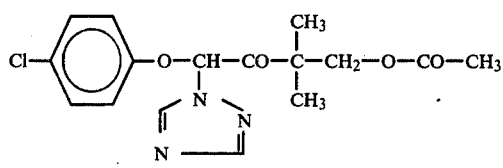

or a salt thereof.

4. A compound according to claim 1, wherein such compound is 4-acetoxy-1-(2,4-dichloro-phenoxy)-3,3-dimethyl-1-(1,2,4-triazol-1-yl)-butan-2-one of the formula

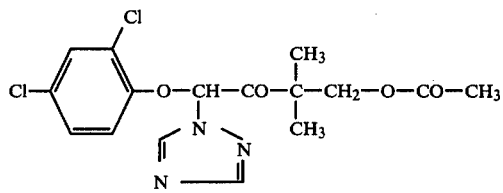

5. A compound according to claim 1, wherein such compound is 4-acetoxy-1-(4-chloro-phenoxy)-3,3-dimethyl-1-(imidazol-1-y)-butan-2-one of the formula

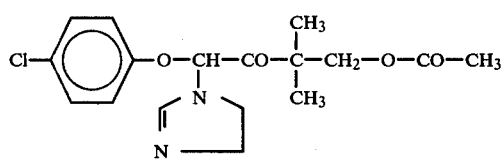

6. A compound according to claim 1, wherein such compound is 1-(4-chloro-phenoxy)-4-hydroxy-3,3-dimethyl-1-(1,2,4-triazol-1-yl)-butan-2-one of the formula

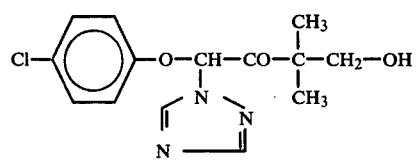

7. A compound according to claim 1, wherein such compound is 1-(4-chloro-phenoxy)-2-hydroxy-3,3-dimethyl-1-(1,2,4-triazol-1-yl)-butan-2-ol of the formula

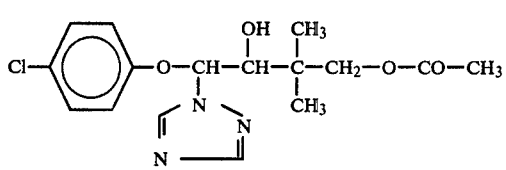

8. A compound according to claim 1, wherein such compound is 4-dichloroacetoxy-1-(4-chloro-phenoxy)-3,3-dimethyl-1-(1,2,4-triazol-1-yl)-butan-2-one of the formula

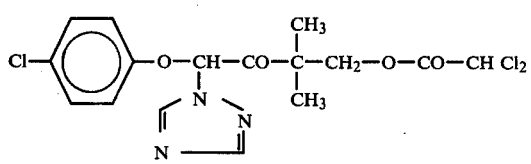

9. A fungicidal or bactericidal composition containing as active ingredient a fungicidally or bactericidally effective amount of a compound according to claim 1 or a salt thereof in admixture with a diluent.

10. A method of combating fungi or bacteria which comprises applying to the fungi or bacteria, or to a habitat thereof, a fungicidally or bactericidally effective amount of a compound according to claim 1 or a salt thereof.

11. The method according to claim 10 in which said compound is
4-acetoxy-1-(4-chloro-phenoxy)-3,3-dimethyl-1-(1,2,4-triazol-1-yl)-butan-2-one,
4-acetoxy-1-(2,4-dichloro-phenoxy)-3,3-dimethyl-1-(1,2,4-triazol-1-yl)-butan-2-one,
4-acetoxy-1-(4-chloro-phenoxy)-3,3-dimethyl-1-(imidazol)-1-yl)-butan-2-one,
(4-chloro-phenoxy)-4-hydroxy-3,3-dimethyl-1-(1,2,4-triazol-1-yl)-butan-2-one,
(4-chloro-phenoxy)-2-hydroxy-3,3-dimethyl-1-(1,2,4-triazol-1-yl)-butan-2-ol, or
4-dichloroacetoxy-1-(4-chloro-phenoxy)-3,3-dimethyl-1-(1,2,4-triazol-1-yl)-butan-2-one,
or a salt thereof.

* * * * *